(12) United States Patent
Zuluaga

(10) Patent No.: US 7,710,569 B2
(45) Date of Patent: May 4, 2010

(54) HEADSET MOUNTED APPARATUS MOUNTING A VISOR WITH INTERCHANGEABLE FILTER SETS

(75) Inventor: Andrés Felipe Zuluaga, Houston, TX (US)

(73) Assignee: Remicalm, LLC, Houston, TX (US)

( * ) Notice: Subject to any disclaimer, the term of this patent is extended or adjusted under 35 U.S.C. 154(b) by 272 days.

(21) Appl. No.: 11/895,788

(22) Filed: Aug. 27, 2007

(65) Prior Publication Data

US 2008/0252893 A1 Oct. 16, 2008

Related U.S. Application Data

(60) Provisional application No. 60/922,823, filed on Apr. 11, 2007, provisional application No. 60/925,222, filed on Apr. 19, 2007.

(51) Int. Cl.
*G01N 21/55* (2006.01)
(52) U.S. Cl. ........................ 356/445; 356/432; 356/442; 600/310; 600/473; 600/476
(58) Field of Classification Search ................. 356/432, 356/442, 445; 600/310, 473, 476, 562
See application file for complete search history.

(56) References Cited

U.S. PATENT DOCUMENTS

| | | | |
|---|---|---|---|
| 4,671,631 A | 6/1987 | Sigelman | 351/205 |
| 4,969,714 A | 11/1990 | Fournier, Jr. et al. | 353/174 |
| 5,479,293 A | 12/1995 | Reed | 359/432 |
| 6,021,344 A | 2/2000 | Lui et al. | 600/476 |
| 6,084,555 A | 7/2000 | Mizoguchi et al. | 345/8 |
| 6,110,106 A | 8/2000 | MacKinnon et al. | 600/181 |
| 7,006,861 B2 * | 2/2006 | Flock et al. | 600/473 |
| 7,532,746 B2 * | 5/2009 | Marcotte et al. | 382/128 |

* cited by examiner

*Primary Examiner*—Gregory J Toatley, Jr.
*Assistant Examiner*—Iyabo S Alli
(74) *Attorney, Agent, or Firm*—Elizabeth R. Hall

(57) ABSTRACT

A portable apparatus having a source, a detector and a filtering element placed a known distance from the source and/or the detector. One embodiment of the apparatus is a headlamp having an illumination source, a camera, and two eye pieces. The headlamp has an adjustable headband for positioning the headlamp on the head of the user and a protective cover for interacting with the camera, eye pieces, and/or illumination source. The protective cover preferably includes multiple sets of filtering elements such that motion about or along an axis changes the filtering elements interacting with the camera, eye pieces, and/or the illumination source.

25 Claims, 8 Drawing Sheets

HEADSET MOUNTED APPARATUS MOUNTING A VISOR WITH INTERCHANGEABLE FILTER SETS

CROSS-REFERENCE TO RELATED APPLICATION

The present application, pursuant to 35 U.S.C. 111(b), claims the benefit of the earlier filing date of provisional application Ser. No. 60/922,823 filed Apr. 11, 2007, and entitled "Filter Set Holder" and provisional application Ser. No. 60/925,222 filed Apr. 19, 2007, and entitled "Headset Mounted Apparatus Mounting a Face Visor with Selectably Interchangeable Optical Filters for Viewing Irradiated Surfaces."

BACKGROUND OF THE INVENTION

1. Field of the Invention

The invention relates to a portable medical examination apparatus having an illumination source, a detector, and a filter set positioned a known distance from the source and/or the detector. More particularly, the present invention relates to a head mounted apparatus having an illumination source, a camera, two eye pieces, and a protective face visor having multiple sets of filtering elements such that motion about or along an axis changes the filtering elements interacting with the camera, the eye pieces, and/or an illumination source.

2. Description of the Related Art

Cervical cancer is the second most common malignancy in women worldwide. The mortality associated with cervical cancer can be reduced if this disease is detected at the early stages of development or at the pre-cancerous state. A pap smear is used to screen the general female population for cervical cancer with more than 70 million performed each year in the United States. In spite of its broad acceptance as a screening test for cervical cancer, pap smears probably fail to detect 50-80% Of low grade cancerous lesions and about 15-30% of high grade lesions.

While the pap smear is designed for initial screening, colposcopy and related procedures are typically used to confirm pap smear abnormalities and to grade cancerous and potential cancerous lesions. Although it is generally recognized that colposcopy is highly effective in evaluating patients with abnormal pap smears, colposcopy has its own limitations. Conventional colposcopy is a subjective assessment based on the visual observation of the clinician and the quality of the results depends greatly on the expertise of the practitioner.

Commercially available colposcopes are large free-standing instruments and are generally maintained in a single location (i.e., one examination room). Furthermore, colposcopes are expensive and are typically shared by multiple doctors. Accordingly, when a colposcopic examination is required, the patient has to be brought to the colposcope. Based on the limited availability of the colposcope, a special appointment time separate from the initial appointment is usually required resulting in additional time and cost to a patient as well as delayed examinations.

Accordingly, a portable apparatus, which allows for a close-up visual medical examination would be advantageous for providing an examination without relocation of the patient or providing a separate appointment time. Such an apparatus would be readily useable and economical, thereby making diagnosis and treatment more readily available and cost efficient.

SUMMARY OF THE INVENTION

One embodiment of the invention is a portable examination apparatus comprising: a head mountable frame; an illumination source mounted on the frame, the illumination source configured to illuminate a tissue with radiation; an illumination filter in operative relation with the illumination source, wherein the radiation generated by the illumination source passes through the illumination filter before illuminating the tissue; a detector mounted on the frame, the detector configured to collect radiation emanating from the tissue illuminated with the illumination source; a detection filter in operative relation with the detector, wherein the radiation emanating from the tissue passes through the detection filter before being collected by the detector; and a selectably operable visor, wherein the visor includes a visor screen that incorporates the illumination filter and the detector filter.

A second embodiment of the invention is a medical examination apparatus comprising: a head mountable frame; an illumination source mounted on the frame, the illumination source configured to illuminate a tissue with radiation; an illumination filter in operative relation with the illumination source, wherein the radiation generated by the illumination source passes through the illumination filter before illuminating the tissue; a detector mounted on the frame, the detector configured to collect radiation emanating from the tissue illuminated with the illumination source; a detection filter in operative relation with the detector, wherein the radiation emanating from the tissue passes through the detection filter before being collected by the detector; two eye pieces mounted on the frame, the eye pieces configured to visualize the radiation emanating from the tissue illuminated with the illumination source; a pair of eye piece filters in operative relation with the eye pieces such that the radiation emanating from the tissue passes through the eye piece filters before passing to the eye pieces; a selectably operable visor, wherein the visor includes a visor screen that incorporates multiple sets of filtering elements, each set of filtering elements includes the illumination filter, the detector filter, and two eye piece filters; and a positioning mechanism for positioning a selected set of filtering elements such that the selected illumination filter is aligned with the illumination source, the selected detector filter is aligned with the detector, and the selected eye piece filters are aligned with the eye pieces.

A third embodiment of the present invention is a portable medical examination apparatus comprising: (a) a head mountable frame; (b) an illumination source mounted on the frame, the illumination source configured to illuminate a tissue with radiation; (c) a detector mounted on the frame, the detector configured to collect radiation emanating from the tissue illuminated with the illumination source; (d) a pair of eye pieces mounted on the frame, the eye pieces configured to visualize the radiation emanating from the tissue illuminated with the illumination source; (e) a visor incorporating a first and a second set of filtering elements in a visor screen, wherein each set of filtering elements includes an illumination filter, a detection filter and two eye piece filters; and (f) a mechanism for reciprocating the visor screen between a first position and a second position, wherein when the visor screen is in the first position the illumination filter of the first set of filtering elements is aligned with the illumination source such that the radiation generated by the illumination source passes through the illumination filter of the first set of filtering elements before illuminating the tissue, the detection filter of the first set of filtering elements is aligned with the detector such that the radiation emanating from the tissue passes through the detection filter of the first set of filtering elements before being collected by the detector, and the pair of eye piece filters of the first set of filtering elements is aligned with the pair of eye pieces such that the radiation emanating from the tissue passes through the pair of eye piece filters of the first set of filtering elements before passing to the eye pieces, and when the visor screen is in the second position the illumination filter of the second set of filtering elements is aligned with the illumination source such that the radiation generated by the illumination source passes through the illumination filter of the second set of filtering elements before illuminating the tissue, the detection filter of the second set of filtering elements is aligned with the detector such that the radiation emanating from the tissue passes through the detection filter of the second set of filtering elements before being collected by the detector, and the pair of eye piece filters of the second set of filtering elements is aligned with the pair of eye pieces such that the radiation emanating from the tissue passes through the pair of eye piece filters of the second set of filtering elements before passing through to the eye pieces.

The foregoing has outlined rather broadly several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

The invention relates to a portable examination apparatus having a head mountable frame, an illumination source, a detector, and a selectably operable protective shield, or face visor. The visor incorporates an illumination filter and a detector filter such that whenever the visor is engaged the illumination filter will interact with the radiation generated by the illumination source and the detector filter will interact with the radiation emanating from a sample illuminated with the illumination source. The term "radiation" is herein defined as "waves or particles such as light, sound, radiant heat, or particles emitted by radioactivity." The term "light" is herein defined as any electromagnetic radiation and includes photons, gamma rays, x rays, ultraviolet radiation, visible light, infrared radiation, microwaves, radio waves, heat, and electric current.

Examination Device 100

Figure 1:
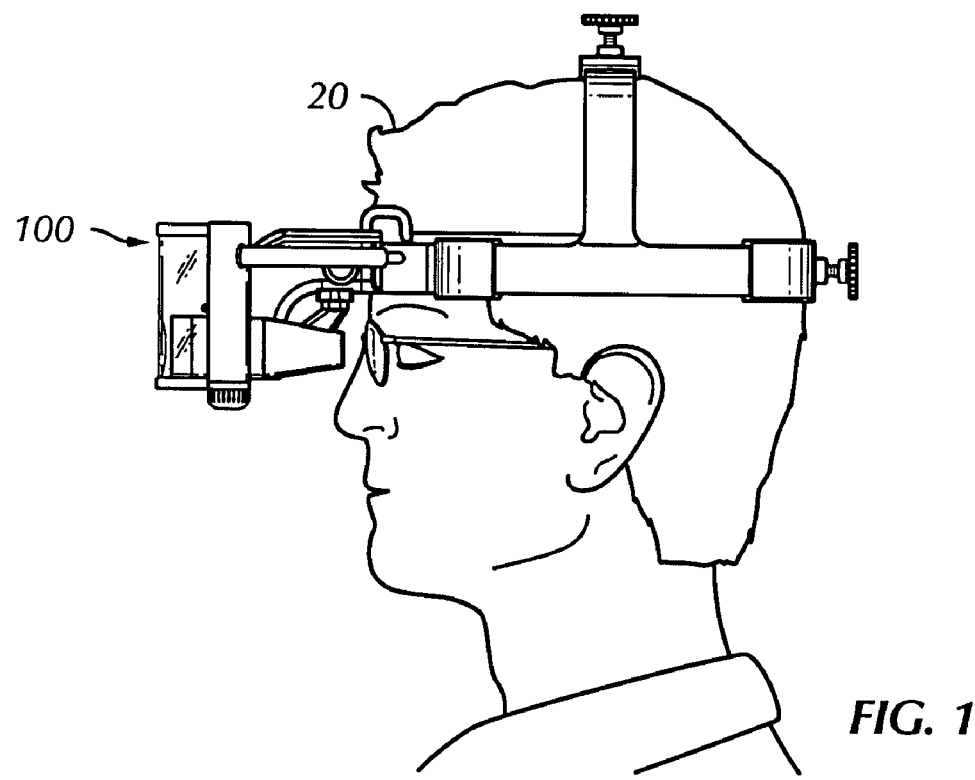
FIG. 1 is a side view of a first embodiment of a medical examination device, wherein the device is mounted on a human head and the visor is in position for filtering light passing through the visor.
Figure 2:
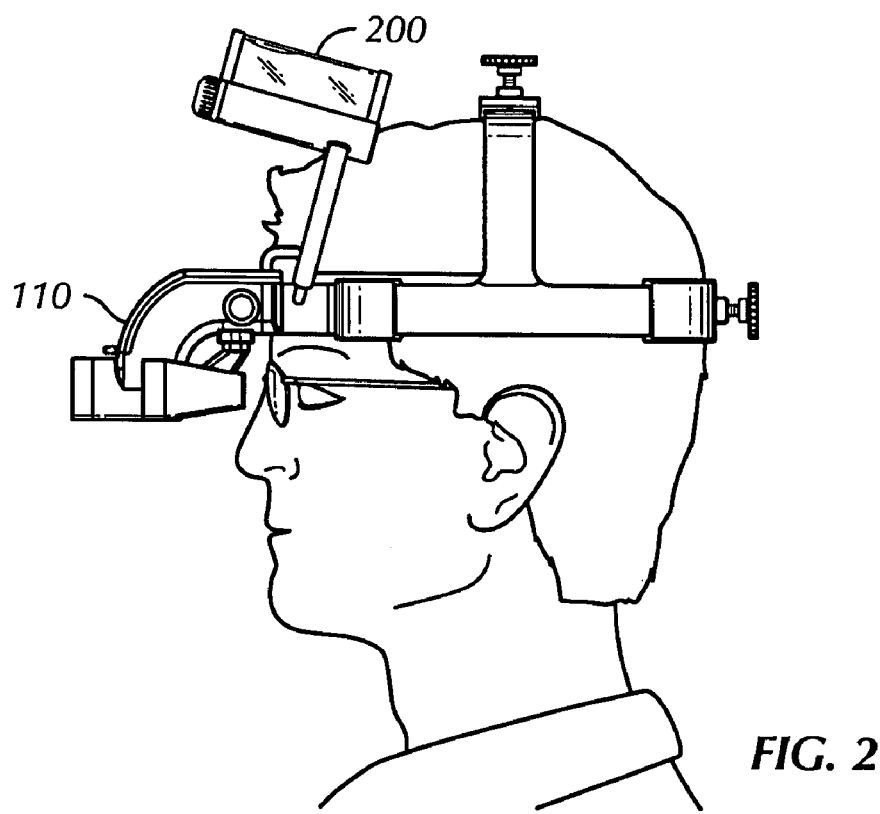
FIG. 2 corresponds to FIG. 1, but shows the visor in position where it is out of the line of vision for the operator.

FIGS. 1 and 2 illustrate a first embodiment of a head mounted examination device 100. The examination device 100 is structured to be positioned on the head of the user or operator 20 as shown in FIG. 1. This allows the operator versatility in positioning and viewing during an examination of a sample such as a tissue sample. The examination device 100 includes a protective shield or visor 200 mounted on a headpiece 110.

The headpiece 110 includes an adjustable head mount and a frame 138 mounting an illumination source 122 and a detector 120.

The adjustable head mount positions the examination device 100 on the head of the operator 20. The head mount includes a thin, flexible plastic ring 112 of an approximately elliptical shape for fitting horizontally on the head of a user. The head mount horizontal ring 112 is provided with padding and has a horizontal adjustment screw 114 for adjusting the effective circumference of the ring to fit different head sizes. A preferred method of making the horizontal adjustment is to split the horizontal ring at the rear of the headpiece and to provide overlapping tabs which can be clamped rigidly together by the adjustment screw mounted in a sleeve enclosing the tabs. A second method of making the adjustment is to split the horizontal ring at the rear of the headpiece and to provide overlapping tabs having racks of gear teeth on their facing horizontal edges. This second means then uses a pinion gear (not a screw) on the shaft of the adjustment means to engage the opposed linear gear racks to cause the effective circumference of the horizontal ring when the adjustment means is rotated. The adjustment means is journaled in a sleeve surrounding the overlapping tabs.

A roughly semicircular across head strap 116 lies in the vertical plane and joins two opposed sides of the horizontal ring 112 by passing over the head near the ears. The across head strap 116 is also provided with a length adjustment of the same type as for the head mount horizontal ring 112. Both these adjustment means enable the flexible head mount to be adjusted to any head so that the illumination source 122, the detector 120, and the optional eyepieces 124 will be correctly aligned for the operator's use. Adjusting the head mount to fit the individual operator will stabilize the headpiece 110 so that the headpiece will maintain its position on the operator's head despite changes of head position.

Figure 3:
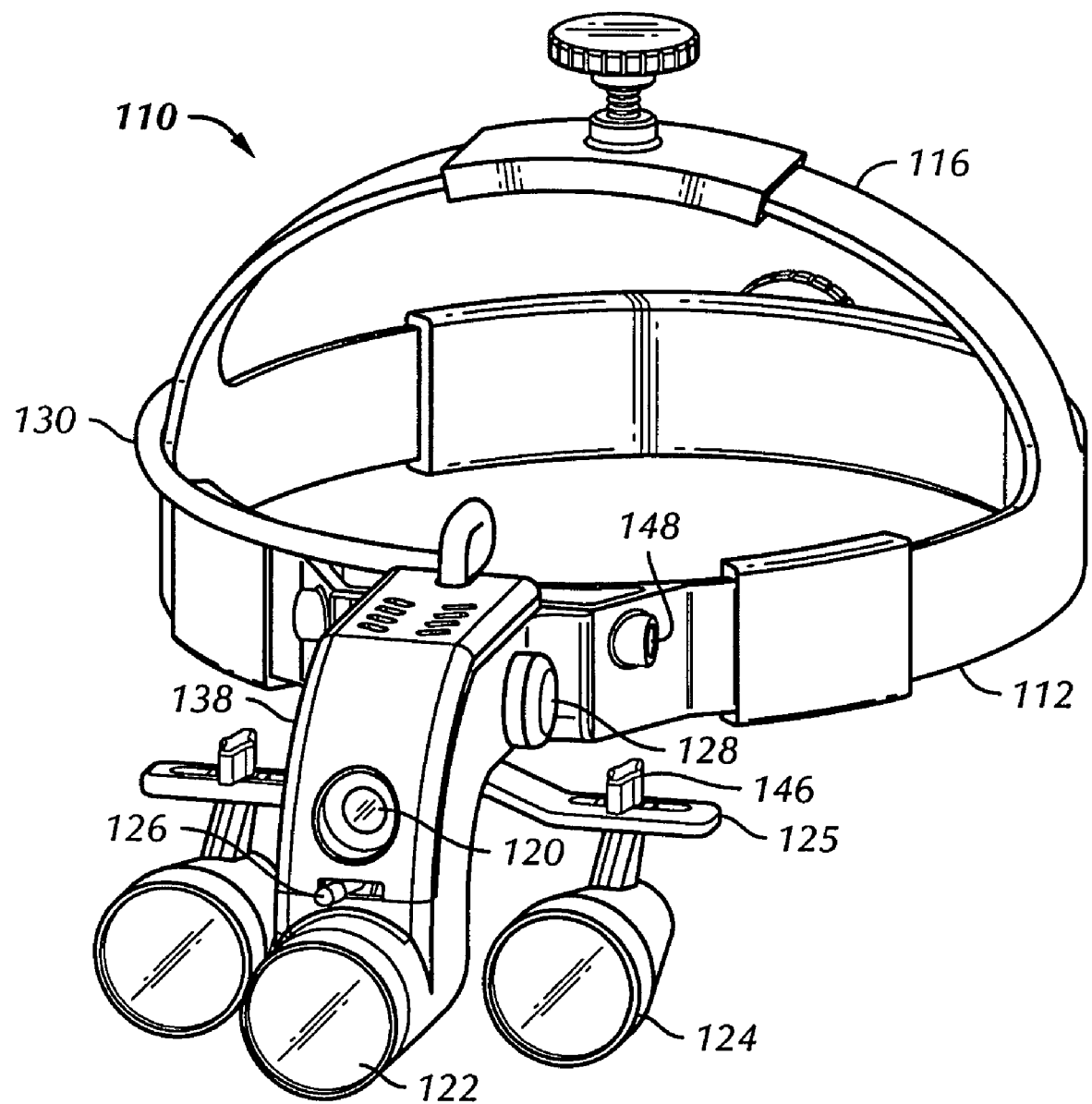
FIG. 3 is an oblique frontal view of the headpiece of the first embodiment of the examination device seen in FIG. 1.
Figure 4:
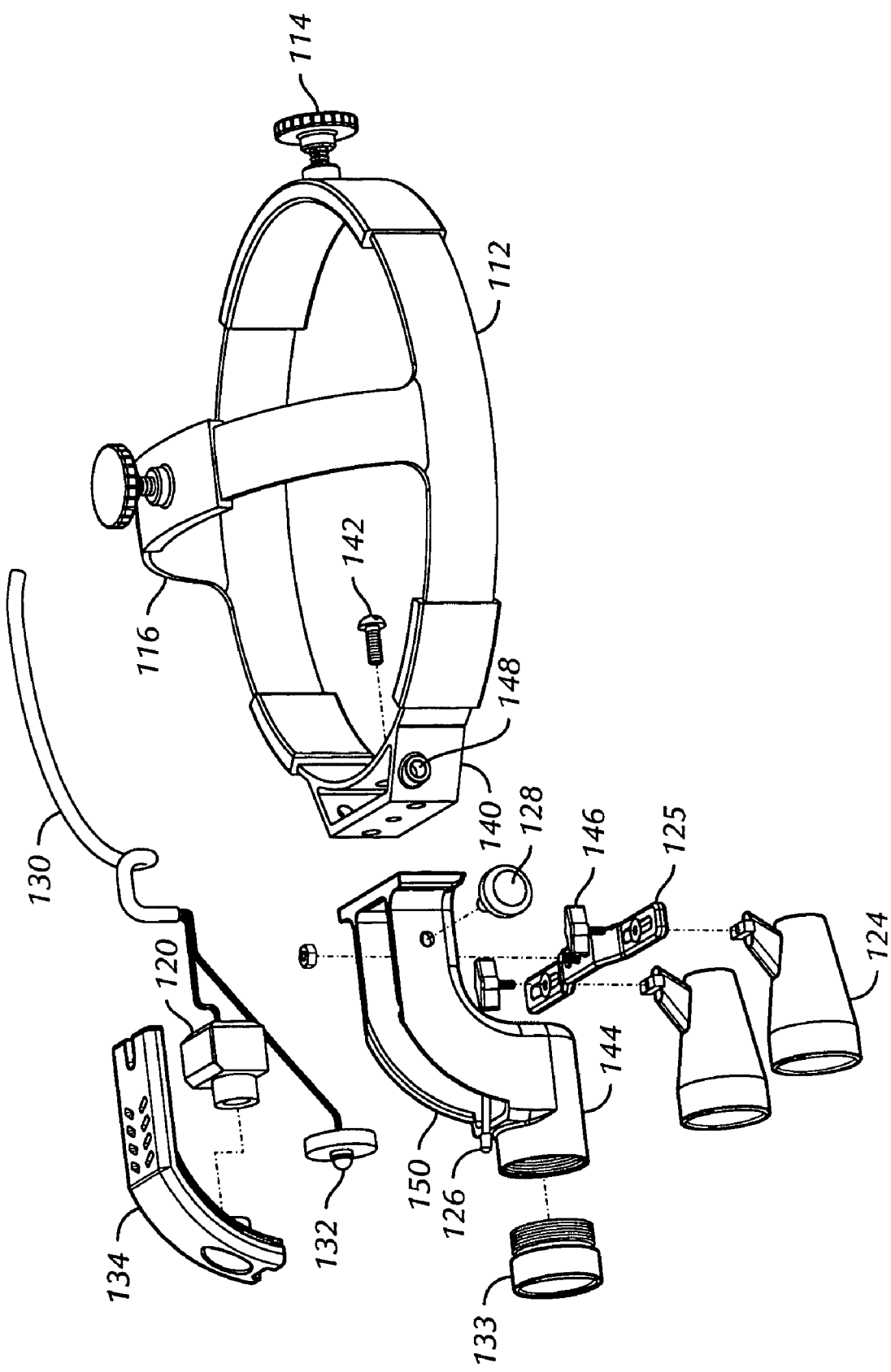
FIG. 4 is an exploded view of the headpiece of FIG. 3.

The frame 138 of the examination device 100 is mounted on the forward side of the adjustable head mount and is typically constructed of relatively rigid injection-molded plastic materials. The frame includes a mounting bracket 140 and a main housing 150 for the attachment of the illumination source 122, as best seen in FIGS. 3 and 4. The mounting bracket 140 is a symmetrical thin element constructed of vertical flat elements. The middle of the mounting bracket is a central flat perpendicular to the long axis of the ellipse of the headpiece ring, and it is joined at its ends to the front of the head mount by two flat side elements angularly offset from the central flat. The central flat has a horizontal axis screw hole at its middle, while a larger coaxial hole in the headpiece horizontal ring 112 provides access to the head of a mounting screw 142 that is engaged through the screw hole and used for attaching the housing 150.

A transverse horizontal hole penetrates both side elements of the mounting bracket 140 above the midheight of the mounting bracket. The penetrations are provided with outwardly extending reinforcing mounting bosses 148.

The main housing 150 provides mounting for an illumination source 122 for illuminating the sample or tissue surface under investigation with radiation, a detector 120 for collecting and/or recording the radiation emanating from the sample illuminated with the illumination source, and a pair of optional eye pieces 124.

The main housing 150 includes a short horizontal open-top section projecting forward from an end bulkhead having two horizontally outwardly extending short transverse rectangular ears. The forwardly projecting open-top section is cojoined by a forwardly and downwardly curving approximately 90° arcuate section having an open side on its outer arcuate side, ending in an intersecting integral forwardly extending tubular emitter housing 144.

An inwardly extending centrally positioned drilled and tapped boss in the end bulkhead permits mounting the main housing 150 to the mounting bracket 140 of the headpiece 110 by means of the mounting screw 142. The trough formed by the horizontal and arcuate sections of the main housing 150 opens into the tubular emitter housing 144. A female helical thread on the forward end of the emitter housing 144 permits the threaded attachment of an emitter lens 133 to assist in focusing the emitted radiation from the illumination source 122 into a narrow beam for impingement onto the tissue sample.

Interior and concentric to the bore of the emitter housing 144 is a transverse disk upon which an outwardly, forwardly facing illumination emitter 132 is mounted. A preferred embodiment uses a light emitting diode (LED) as the illumination emitter 132, as shown in FIG. 4. The LED is selected to emit light with a desired predominant wavelength. The emitter lens 133 focuses the emitted light into a narrow beam which is projected forward. An adjustment lever or mechanism 126 is horizontally positioned above the emitter housing 144 to serve as a means of focusing the light beam of the LED (mechanism not shown).

A preferred embodiment of the examination device 100 has two eye pieces 124 attached to the main housing 150 as illustrated in FIGS. 3 and 4. The eye pieces 124 have a field of view that is substantially similar to the field of view of the detector. An eye piece support bar 125, mounted transversely to the main housing 150 on its lower horizontal side, is generally symmetrical about the vertical longitudinal midplane of the examination device 100. A vertical hole on the lower horizontal side of the horizontal segment of the main housing 150 permits the attachment of an eye piece support bar 125 by means of a screw and nut. The eye piece support bar 125 has an elongated constant cross-section with a horizontal midsection having a central vertical through hole for mounting purposes and downwardly offset horizontal outwardly extending arms having elongate slots for mounting of an eye piece 124 on each end of the eye piece support bar 125. The axes of the eye pieces 124 are preferably mounted at about the same elevation as the axis of the tubular emitter housing 144.

Preferably two eye pieces 124 are used, one for each eye, with the eye pieces symmetrically positioned on opposed ends of the eye piece support bar 125 as shown in FIGS. 3 and 4. The eye pieces 124 typically have short right circular cylindrical outer ends cojoined by frustroconical inner end segments which reduce in size towards the head mount. The eye pieces 124 have inclined pylons upwardly extending in a radial plane. The eye piece pylons have a distal transverse horizontal projection for maintaining alignment of the eyepiece perpendicular to the horizontal axis of the slots of the eyepiece support bar 125. The upper ends of the pylons are provided with vertical drilled and tapped holes so that each eye piece 124 can be mounted to the eyepiece support bar 125 by means of a clamp screw 146. The slots of the eyepiece support bar 125 permit the eye pieces 124 to be aligned with the individual eyes of an observer 20. Preferably, the eye pieces 124 are provided with internal lenses to provide magnification for their field of view.

A small forwardly facing detector 120 is mounted inside the main housing 150 to record the image of the illuminated surface. The detector 120 collects and/or records the radiation emanating or reflected from the tissue illuminated with the illumination source 122. A preferred embodiment of the detector 120 is a digital camera, although the detector 120 may also be a television camera or a conventional still camera. One embodiment of the examination device 100 will couple the camera with an imaging element (not shown).

Both the detector 120 and the illumination emitter 132 are provided with power by means of a communication cable 130 having power cords for the detector 120 and illumination emitter 132. In a preferred embodiment, the communication cable 130 will include a power cord for the detection camera, a communication cord for the imaging element, and a power cord for the LED illumination emitter 132.

A horizontal hole penetrates the side of the main housing 150 at approximately midheight near to the end bulkhead. This horizontal hole serves to mount a detector focus knob 128 which extends into the interior of the main housing 150. The detector focus knob 128 engages a focusing mechanism (not shown) for the detector 120 which is mounted in the interior of the main housing 150.

A cover 134 is provided for the open-top section of the main housing 150. The cover 134 has a horizontal inner end and an arcuate outer end. The flat horizontal inner section of the cover 134 is engaged structurally to the top flat open-top section of the main housing 150 by means of a snap fit between the grooves of the main housing 150 and outwardly extending male ridges on vertical projections of the cover 134. The opposed arcuate interior vertical walls of open-top arcuate section of the main housing 150 have grooves adjacent their outer arcuate edges for engagement with comateable ridges provided with the arcuate outer end of the cover 134.

The inner distal end of the cover 134 has a short central notch for permitting passage of the communication cable 130. The arcuate outer end of the cover 134 has an aperture for the detector 122. For embodiments of the examination device 100 using a camera as the detector 122, this aperture has an inwardly extending cylindrical boss concentric with the lens of a camera when the cover 134 is assembled to the main housing 150.

Figure 5:
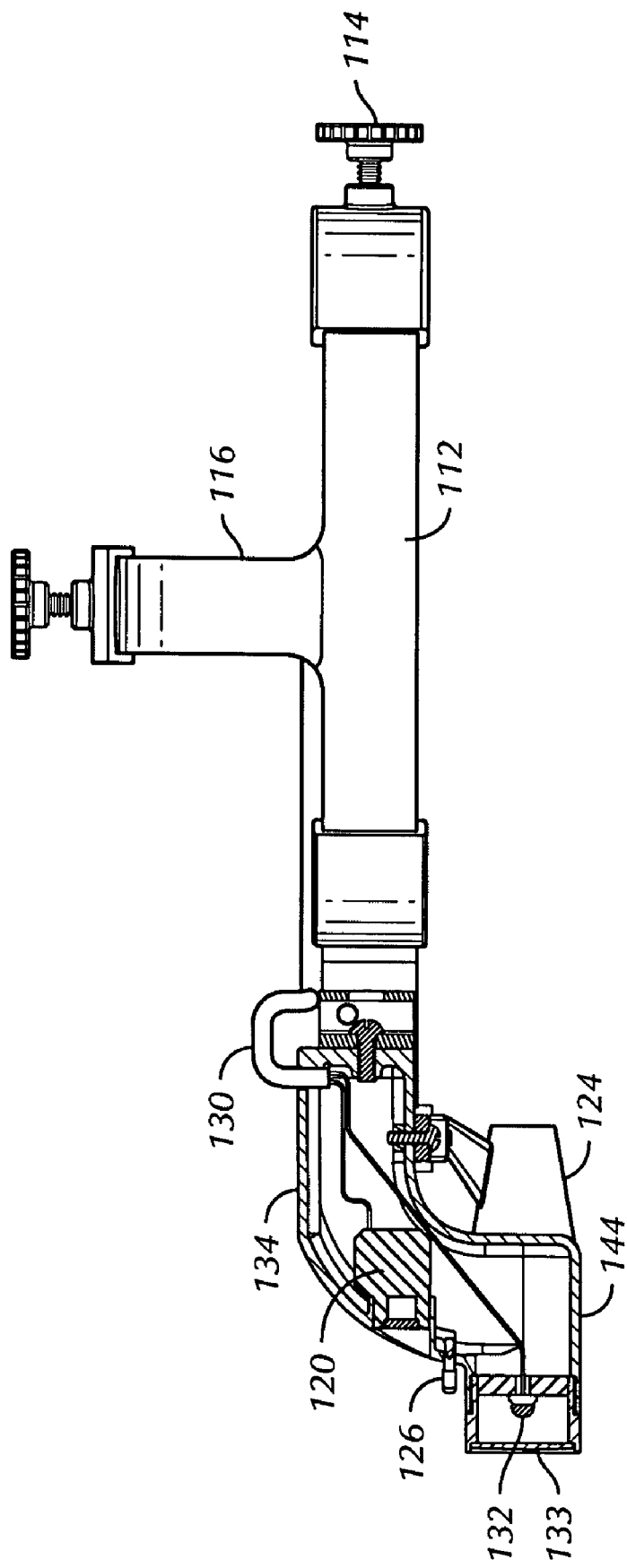
FIG. 5 is a partial vertical longitudinal section of the headpiece of FIG. 3, wherein the housing and the front portion of the headpiece are sectioned.

The inner distal end of the cover 134 is perforated with multiple slots to permit cooling of the interior of the main housing 150. The partial longitudinal vertical cross-section of the lamp unit and mounting bracket of the headpiece shown in FIG. 5 indicates the relative positions of the elements of the assembled headpiece 110.

Figure 6:
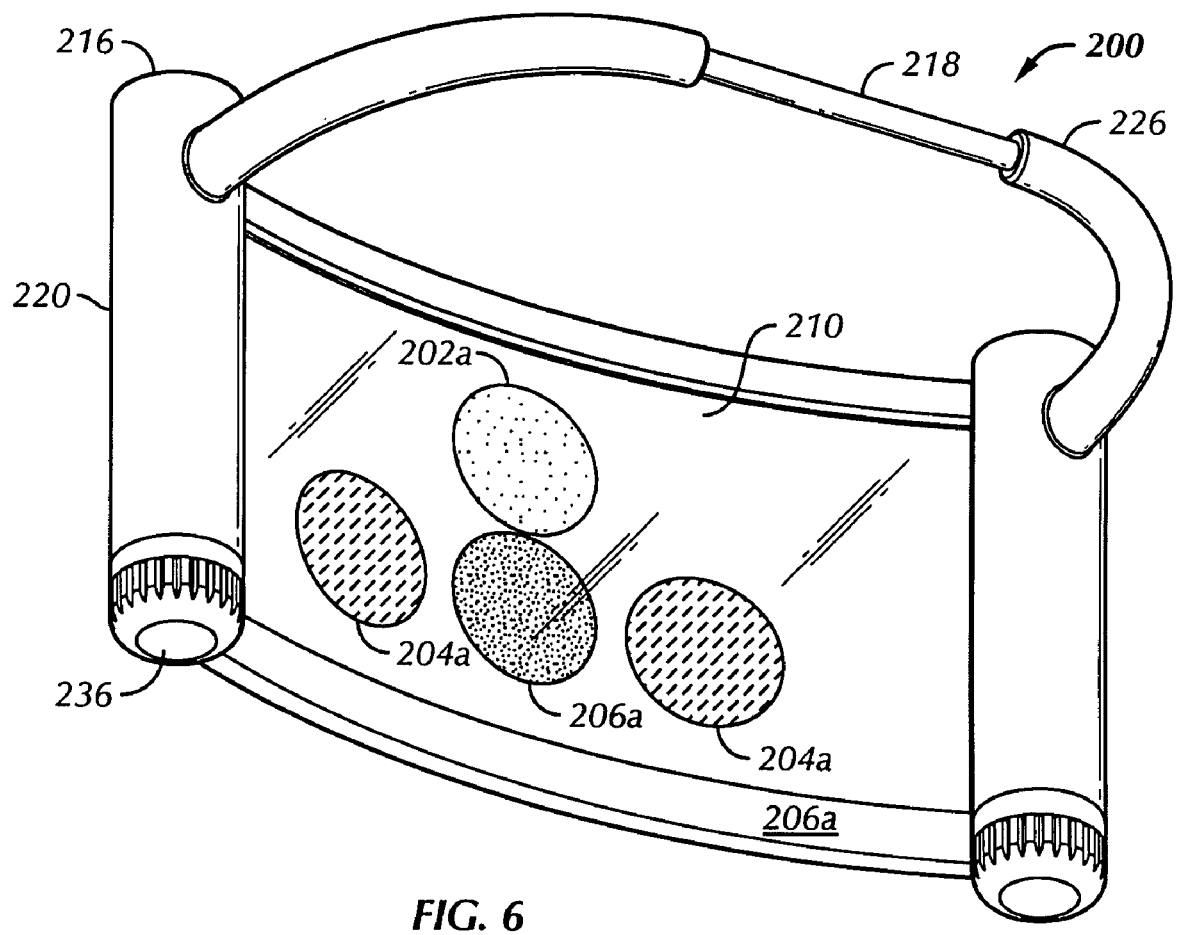
FIG. 6 is an oblique rear view of the visor for the examination device of FIG. 1, wherein the visor screen is selectably scrolled so that a set of filters are arranged to provide filtering for light passing through the visor.

One embodiment of the visor 200, shown in FIG. 6, is typically made of a clear semirigid plastic sheet. The visor screen 210 has at least an illumination filter 206a and a detector filter 202a embedded in the visor screen 210. A preferred embodiment of the visor 200 includes two eye piece filters 204a. The filters are also made of a clear semirigid plastic sheet having the same stiffness properties as those of the visor screen 210. Although the filters may be transparent, the filters are generally configured to select the passage of a particular wavelength of radiant energy. For example, the eye piece filters 204a may be modified to allow the passage of a certain wavelength of visible electromagnetic radiation, or the illumination filter 206a may be modified to pass only ultraviolet light or some other desired wavelength. The visor 200 may also have an optional triggering mechanism for signaling the detector 220 and/or the illumination source 122 of the position of the visor screen 210 and the filters aligned with the detector 220 and/or the illumination source 122.

Figure 8:
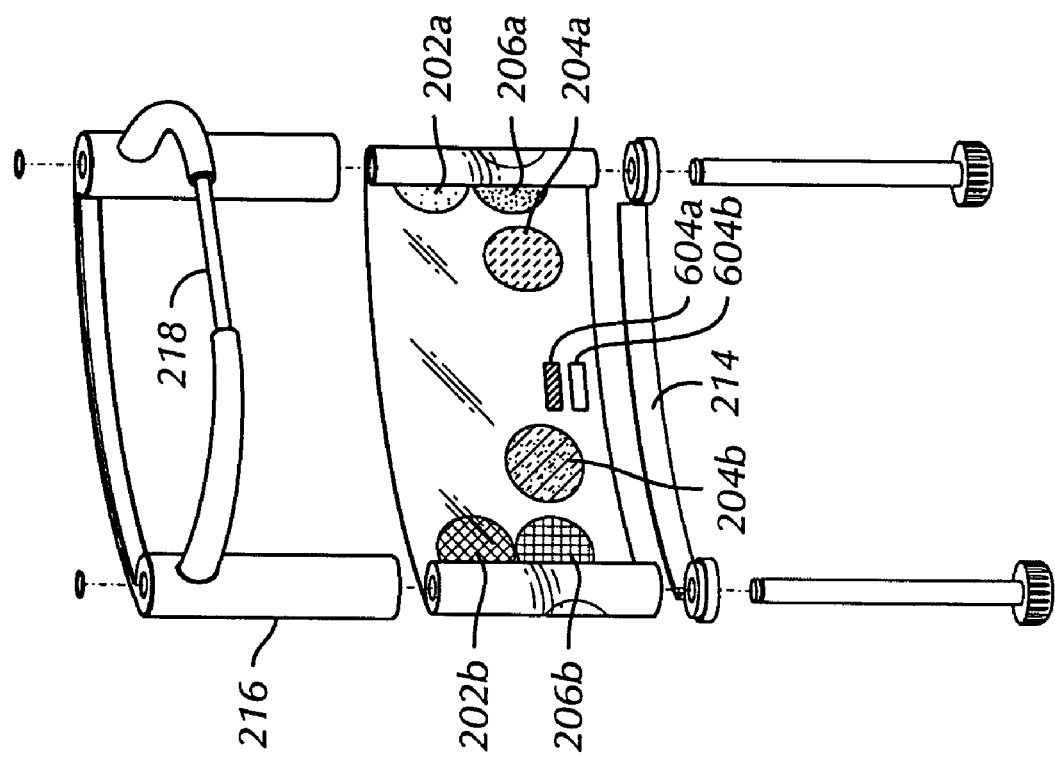
FIG. 8 corresponds to FIG. 7, but has the visor screen scrolled so that a second set of filters are in an active, exposed position.
Figure 7:
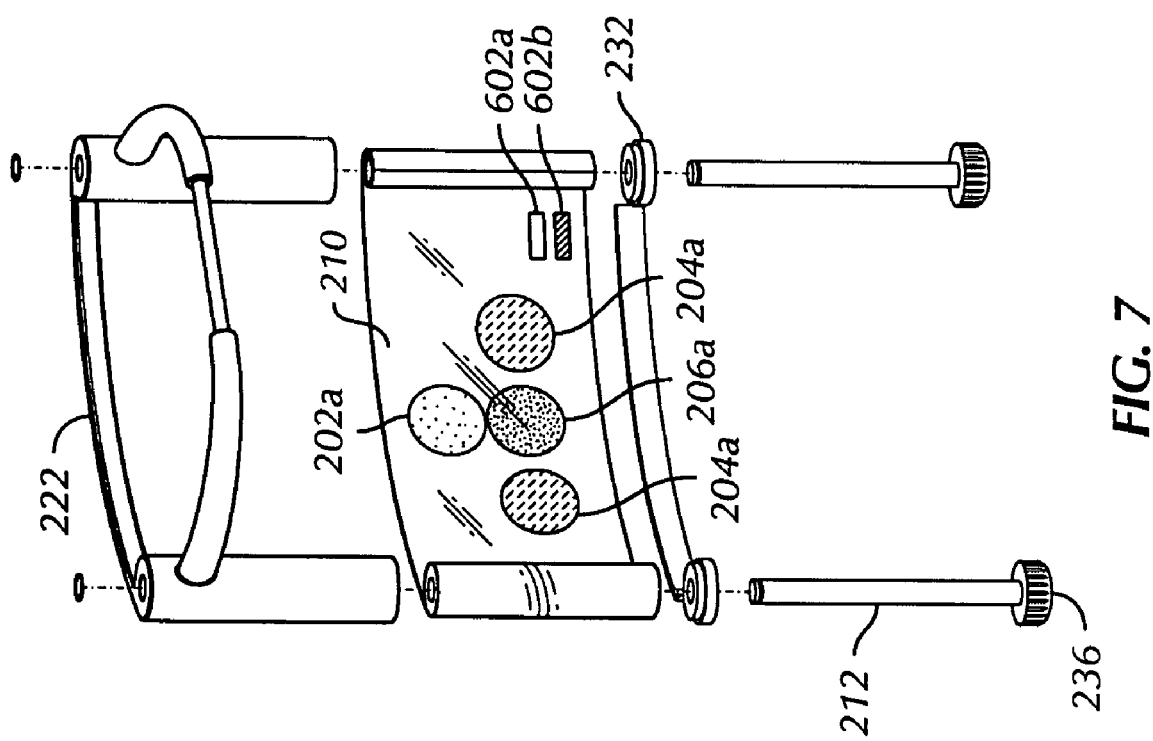
FIG. 7 is an exploded view of the visor of FIG. 6, wherein the visor screen is scrolled to position a first set of filters in an active, exposed position.

The visor 200 is seen in an oblique rear view in FIG. 6 and in exploded views in FIGS. 7 and 8. The visor 200 consists of a frame 220 symmetrical about a vertical midplane and having two vertical roll housings 216, a lower horizontal arcuate track 214, a left and a right spindle 212, and a spoolable flexible transparent visor screen 210 having integral filter elements.

The frame 220 has a horizontal arcuate upper track 222 having the same curvature as the lower arcuate track 214, wherein the upper track 222 cojoins the opposed vertical roll housings 216. Each roll housing 216 has an open lower end and an upwardly opening central hole which journals the upper end of the shaft of the spindle 212.

Symmetrically opposed horizontal arcuate support arms 226 extend straight back and then curve inwardly so that they are normal to and outwardly offset from the vertical midplane of the frame 220. The opposed inwardly facing ends of the support arms are provided with opposed holes which house a horizontal shaft 218 which cojoins the two support arms. The horizontal shaft 218 is deployed in the transverse penetrations reinforced with the mounting bosses 148 in the mounting bracket 140 of the headpiece 110 so that the visor can be pivoted selectably between its operating position shown in FIG. 1 and its retracted position shown in FIG. 2.

The lower track 214 is a mirror image of the upper track 222, and both tracks have arcuate horizontal grooves for guiding engagement and support of the horizontal edges of the spoolable visor screen 210. The distal ends of the lower track have short stepped integral right circular cylinders 232, wherein the smaller diameters of the cylinders are snuggly engaged into the bores of the roll housings 216 for retention and the larger diameters are the same as the outer diameters of the roll housings. The cylinders of the lower track have coaxial through holes which journal the shafts of the spindles 212.

The roll housings 216 have vertical exit slots which are aligned with the horizontal grooves of the upper and lower tracks. The spindles 212 have elongate vertical right circular cylindrical shafts with a snap ring groove at their upper ends and manual rotation knobs at their lower ends. The central portions of the spindles 212 are provided with clamps or slots for fixedly engaging the opposed vertical ends of the spoolable visor screen 210. The spoolable visor screen is engaged between the upper ends of the roll housings 216 and the upper ends of the cylinders 232 of the lower track 214, while the knobs of the spindles 236 are exposed on the lower side of the lower track. The spindles 212 are retained by snap rings in their upper grooves, as seen in FIGS. 7 and 8.

In a preferred embodiment of the visor 200 a set of three holes in a horizontal plane with an upwardly vertically offset central hole house four filters at one or more positions in the spoolable visor screen 210. The filters are generally treated to selectively pass only certain wavelengths of light. Although the filters may be any shape, the detector filter 202a and/or the illumination filter 206a are typically circular in shape when flat. The eye piece filters 204a may also be circular, but may they will often take on an elliptical shape to account for some variation in the positioning of the eye pieces 124.

The visor screen 210 contains one or more set of filters. For example, FIG. 6 illustrates a set of four filters (i.e., two eye piece filters 204a, an illumination filter 206a, and a detector filter 202a). These filters are positioned so that, when spooled into position the illumination filter 206a is located directly in front of the illumination emitter 132, the eye piece filters 204a are positioned directly in front of the eye pieces 124, and the detector filter 202a is positioned directly in front of the detector 120. Different filters are generally used for the two eye piece filters 204a, the illumination filter 206a, and the detector filter 202a depending on the wavelength of radiation selected for emission and the wavelength desired for observation.

The use of multiple sets of filters embedded in a scrollable visor screen 210 permits multiple types of observation with the same visor 200. In order to change the wavelengths for a different type of inspection or observation, the observer 20 can spool the visor screen 210 to select the desired filter set or no filter set. FIGS. 7 and 8 show the visor screen having at least two sets of filters. The first filter set shown in FIG. 7 includes two eye piece filters 204a, an illumination filter 206a, and a detector filter 202a. As the visor screen 210 is spooled toward the right in FIG. 8, a second set of filters begins to appear (i.e., two eye piece filters 204b, an illumination filter 206b, and a detector filter 202b).

An optional feature of visor 200 is to have a mechanical, electronic and/or electromechanical signal for specific filter sets embedded in the visor screen that will trigger configuration changes in the illumination source 122 and/or detector. For example, FIGS. 7 and 8 illustrate a simple system for signaling between two filter sets. FIG. 7 illustrates two horizontal bars to the right of the first set of filters 202a, 204a and 206a. The upper bar 602a is transparent and the bottom bar 602b is made of a metallic conductive material. FIG. 8, on the other hand, illustrates two horizontal bars to the right of the second set of filters 202b, 204b and 206b. The upper bar 604a is the metallic conductive material and the bottom bar 604b is transparent.

Thus, when the first filter set is in position the metal conductive material of the lower bar 602b can complete a circuit to signal turning on a switch to activate a predetermined illumination source configuration and/or a detector configuration. For example, the signal may activate a first light source (e.g., a particular LED of several LEDs) in the illumination source and/or a predetermined operating condition for the light source (e.g., a predetermined wattage). The signal may also activate a first detector (e.g., a particular detector of several detectors) or a particular detector configuration (e.g., a particular exposure time for the detector). In contrast, when the second filter set is in position the metal conductive material of the upper bar 604a will signal the turning on of a switch to activate a second light source and/or operating condition of the illumination source and/or a second detector and/or configuration of the detector.

Examination Device 400

Figure 9:
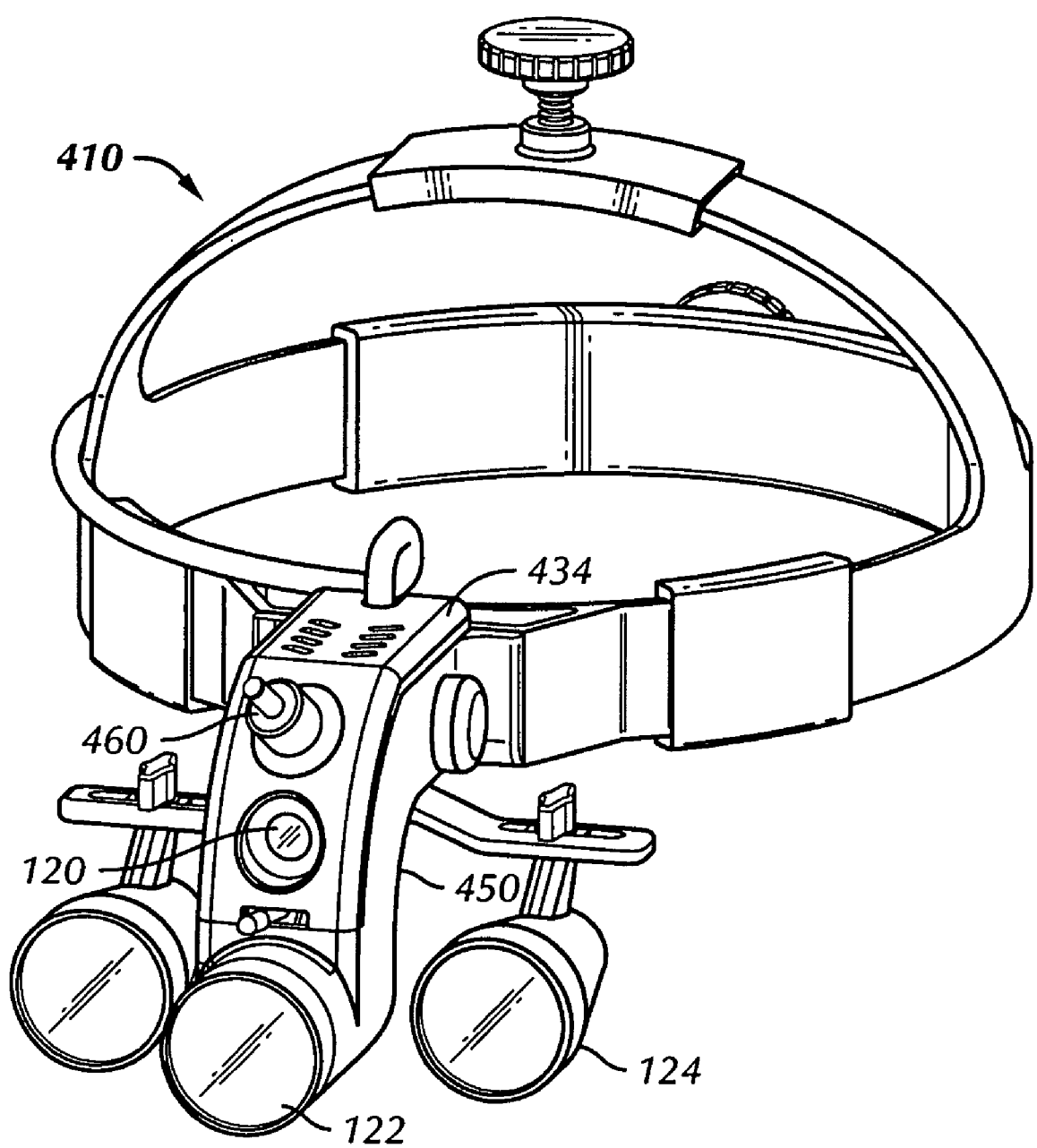
FIG. 9 is an oblique frontal view showing the headpiece of a second embodiment of the medical examination device.

A second embodiment of the examination device 400 is shown in FIGS. 9-13. The primary structural components of the headpiece 410 of the examination device 400 are basically the same as for the examination device 100, except that the visor 500 is mounted and arranged differently than for the examination device 100. The structural difference for the headpiece 410 is the elimination of the transverse holes through the mounting bracket 140 for the support of the shaft 218 of the visor 200, rather the cover 434 for the headpiece 410 has a reinforcing boss on the longitudinal midplane projecting outwardly at an angle from the horizontal and supporting a coaxial centrally positioned inclined pivot shaft 460, as seen in FIG. 9. Otherwise, the headpiece 410 and the main housing 450 are the same as for the examination device 200.

The visor 500 also differs from the visor 200. The visor 500 is a concave arcuate element formed by rotating a symmetrical cross-section equal amounts in both directions about a horizontal transverse axis so that the visor extends over approximately 100° to 120°. The cross-sectional profile can have a constant width or, alternatively, it can be tapered to reduce in width towards its distal ends. The symmetrical cross-section can be either a circular arc, a portion of an elliptical profile, or a straight central segment with inwardly inclined straight or curved side segments. The intersection of the two planes of symmetry of the visor 500 forms an axis of rotation for the visor. A short inwardly extending cylindrical boss 510 has a central coaxial cylindrical hole which closely fits the pivot shaft 460 mounted on the cover 434 of the main housing 450.

The visor 500 is provided with one or more sets of holes in the same pattern as those in the first visor so that sets of filters can be mounted therein. The material of the second visor is a transparent rigid plastic. As the case for the filters of the first visor, the second filters are of the same material as the second visor, but with the addition of either surface coatings or modifications so that they selectively pass only certain wavelengths of light.

Figure 10:
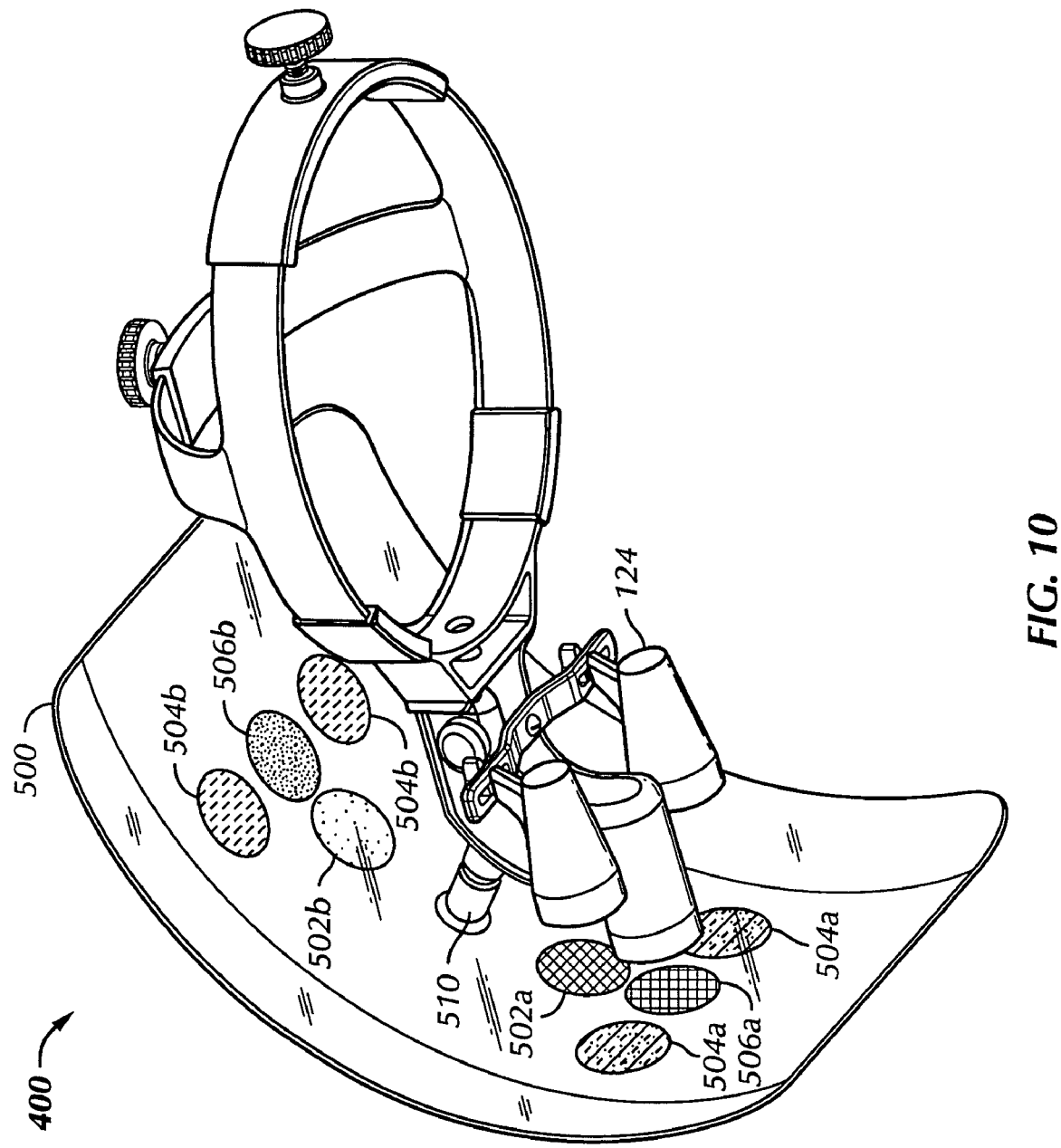
FIG. 10 is an oblique rear view of the visor for the examination device of FIG. 9, wherein the visor screen is.

The visor 500 contains one or more filter sets. For example, FIG. 10 illustrates visor 500 with two filter sets. The first set is shown in position such that the two eye piece filters 504a are positioned directly in front of the eye pieces 124, the illumination filter 506a is located directly in front of the illumination source 122, and the detector filter 502a is positioned directly in front of the detector 120. Different filters are generally used for the two eye piece filters, the illumination filter, and the detector filter depending on the wavelength of radiation selected for emission and the wavelength desired for observation.

The use of multiple sets of filters permits multiple types of observation with the same visor 500. In order to change the wavelengths for a different type of inspection or observation, the observer 20 can rotate the visor 500 about the pivot shaft 460 to select the desired filter set or no filter set. FIG. 10 shows the visor 500 having two sets of filters. The first filter set shown in FIG. 10 includes two eye piece filters 504a, an illumination filter 506a, and a detector filter 502a. As the visor 500 is rotated about the pivot shaft 460, a second set of filters can be positioned for observation (i.e., two eye piece filters 504b, an illumination filter 506b, and a detector filter 502b).

An optional feature of visor 500 is to have a mechanical, electronic and/or electromechanical signal for specific filter sets embedded in the visor screen that will trigger configuration changes in the illumination source 122 and/or detector. For example, the rotation of the visor 500 and its boss 510 could rotate the pivot shaft 460 and mechanically change the configuration of the illumination source and/or detector. The configuration changes induced by the rotation of the pivot shaft 460 can change the type of illumination source (e.g., visible to ultra violet illumination) and/or detector (e.g., digital camera to a television camera), or rotation of the shaft can change the settings of the illumination source (e.g., the wattage going to an LED illumination source) and/or the detector (e.g., the exposure time or zoom on a digital camera).

Operation of the Invention

The operation of the two embodiments illustrated is identical in most respects, differing only in the adjustment of the visor for using different filter sets. The first examination device 200, shown in FIGS. 1 to 8, and the second examination device 400, shown in FIGS. 9 and 10, operate the headpiece identically.

When a new observer 20 dons the examination device, he adjusts the lengths of the across head band 116 and the around head band 112 so that the device snuggly fits his head and the axes of the eyepieces are properly aligned with his eyes. If necessary, the offset of the eyepieces from the midplane can be adjusted by loosening the clamp screws, shifting the eyepieces laterally down the slots of the eye piece support bar, and then reclamping.

Normally, power for operating the device is provided by a battery pack (not shown) mounted on a belt or free standing and connected to the viewing device by the power cord. The power can be switched on by a switch on the battery pack. However, the device may also have a cord for plugging the examination device into a power outlet.

When the power is switched on, the visor is moved into its viewing position and the desired filter set is positioned in front of the apertures of the examination device. With the visor 200 the filter set is positioned by appropriately rotating the knobs of the spindles 212 of the visor 200. The visor 200 can be raised at any time for unobstructed viewing and then selectably returned to its operational position, as seen in FIGS. 1 and 2. In the case of the visor 400 the filter set is positioned by rotating the visor 400.

Once the visor is positioned and the proper filter set is aligned with the appropriate illumination source and detector, the focus of the illumination source and the detector can be independently adjusted using the adjustment mechanism 126 and the camera focus knob 128. When illumination sources and/or detectors are used that do not require focusing, the adjustment mechanism 126 and/or the focus knob 128 may not be necessary.

Depending upon which set of filters, if any, is present in front of the viewing device, the emitted light from the illumination emitter 132 passes through the middle illumination filter 206a in the lower set of three filters. The beam of this filtered light strikes the tissue sample to be observed. The impinging light is partially reflected, and some of the light may cause fluorescence on the surface of the observed object. Some portion of the reflected light and any fluorescence impinge on the right and left filters of the visor, with a portion of the this impinging light selectively passing through those filters to the eyepieces and thence to the eyes of the observer.

Similarly, another portion of the reflected light and any fluorescence will impinge on the upper detector filter 202a in the filter set of the visor 200. This filtered light is selectively filtered by the detector filter and then sensed by the detector.

The operation of the examination device 400 is substantially similar to the operation of the examination device 200 except for the operation of the visor 500. The visor 500 is selectably rotated about the pivot shaft 460 seen in FIG. 9 so that the desired filter set is in alignment with the axes of the apertures of the viewing device. The visor 500 can also be rotated so that no filtering is provided by the visor 500. As is the case for the first visor, when a filter set is aligned with the lamp assembly, the emitted light is filtered. Any light emanating from, reflected from and/or fluorescing from the illuminated surface is filtered when passing through the right and left filters to the eyepieces and by the detector filter when passing through to the detector.

For both embodiments, the visors also promote sanitation by providing a degree of isolation between the observer and the observed surface.

Advantages of the Invention

The examination devices of the present invention offer a simple, inexpensive, convenient, and effective means of using various wavelengths of light, including ultraviolet light, for the visual inspection of a surface. The viewing devices are light weight, generally robust in construction, and easy to clean and service. The provision of a visor provides a sanitary and protective barrier between the observer and the viewed object surface. One advantage of the examination devices is their simple positioning adjustment for the alignment of different filter sets for the emitted and received light beams. An additional advantage is the easy means of adjusting the visor so that the viewed object surface can be seen without filtering.

It should be appreciated by those skilled in the art that the conception and the specific embodiment disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

What is claimed is:

1. A portable examination apparatus comprising:
   a head mountable frame;
   an illumination source mounted on the frame, the illumination source configured to illuminate a tissue with radiation;
   a detector mounted on the frame, the detector configured to collect radiation emanating from the tissue illuminated with the illumination source; and
   a selectably operable visor having a visor screen embedding an illumination filter and a detector filter, wherein movement of the visor screen concurrently moves the illumination filter and the detector filter between an aligned position and a non-aligned position, wherein the aligned position aligns the illumination filter and the detection filter with the illumination source and the detector respectively and the non-aligned position moves the illumination filter and the detection filter out of alignment with the illumination source and the detector respectively.

2. The apparatus of claim 1, wherein the head mounted frame is adjustable.

3. The apparatus of claim 1, wherein the illumination source is a LED.

4. The apparatus of claim 1, wherein the detector is a camera.

5. The apparatus of claim 1, further comprising an adjustment mechanism for focusing the radiation pattern generated by the illumination source.

6. The apparatus of claim 1, further comprising two eye pieces mounted on the frame.

7. The apparatus of claim 6, wherein a field of view of the two eye pieces and the detector is substantially similar.

8. The apparatus of claim 1, wherein a distance between the eye pieces is adjustable.

9. The apparatus of claim 6, wherein the visor screen further embeds an eye piece filter for each eye piece in a fixed position relative to the illumination filter and the detector filter.

10. The apparatus of claim 6, wherein the visor screen embeds multiple sets of filtering elements, wherein each set of filtering elements includes the illumination filter, the detector filter, and two eye piece filters and wherein whenever the visor screen is moved between the aligned position and the non-aligned position all of the filtering elements within each set of filtering elements are concurrently either aligned or non-aligned with the illumination source, the detector, and the two eye pieces.

11. The apparatus of claim 10, wherein each set of filtering elements is embedded into a first surface of the visor screen.

12. A medical examination apparatus comprising:
    a head mountable frame;
    an illumination source mounted on the frame, the illumination source configured to illuminate a tissue with radiation;
    a detector mounted on the frame, the detector configured to collect radiation emanating from the tissue illuminated with the illumination source;
    two eye pieces mounted on the frame, the eye pieces configured to visualize the radiation emanating from the tissue illuminated with the illumination source;
    a selectably operable visor having a visor screen embedding multiple sets of filtering elements, each set of filtering elements includes an illumination filter, a detector filter, and two eye piece filters in a fixed relationship to each other, wherein the visor screen is selectably movable to any one of a multitude of positions and wherein movement of the visor screen from one position to another position concurrently moves all of the filtering elements of each set of filtering elements and maintains the fixed relationship of the filtering elements within each set of filtering elements.

13. The examination apparatus of claim 12, wherein the illumination source includes a first light source and a second light source and wherein the visor screen includes a first signal embedded in the visor screen in a fixed relationship to a first set of filtering elements such that when the visor screen is in a first position the first signal enables the first light source and wherein the visor screen includes a second signal embedded in the visor screen in a fixed relationship to a second set of filtering elements such that when the visor screen is in a second position the second signal enables the second light source.

14. The examination apparatus of claim 12, wherein the illumination source includes multiple LEDs and wherein the visor screen fixedly embeds a signal associated with each set of filtering elements such that when a selected set of filtering elements is positioned to align the illumination filter of the selected set with a predetermined LED the embedded signal associated with the set of filtering elements including the aligned illumination filter activates the predetermined LED.

15. The examination apparatus of claim 12, wherein the illumination source includes a predetermined operating condition for each set of filtering elements embedded in the visor screen and wherein the visor screen further includes a signal associated with each set of filtering elements fixedly embedded in the visor screen such that when one set of filtering elements is selected and positioned to align the illumination filter of that set of filtering elements with the illumination source, the signal associated with the selected set of filtering elements activates the predetermined operating condition of the illumination source for the selected set of filtering elements.

16. The examination apparatus of claim 12, wherein the detector includes a first configuration and a second configuration and wherein the visor screen includes a first signal embedded in the visor screen in a fixed relationship to a first set of filtering elements such that when the visor screen is in a first position the first signal enables the first configuration of the detector and wherein the visor screen includes a second signal embedded in the visor screen in a fixed relationship to a second set of filtering elements such that when the visor screen is in the second position the second signal enables the second configuration of the detector.

17. The examination apparatus of claim 12, including a first detector and a second detector and wherein the visor screen includes a first signal embedded in the visor screen in a fixed relationship to a first set of filtering elements such that when the visor screen is in a first position the first signal enables the first detector and wherein the visor screen includes a second signal embedded in the visor screen in a fixed relationship to a second set of filtering elements such that when the visor screen is in a second position the second signal enables the second detector.

18. The examination apparatus of claim 12, wherein the detector is a camera having a predetermined configuration for each set of filtering elements and wherein the visor screen includes a specific signal embedded in the visor screen associated with each set of filtering elements such that when a selected set of filtering elements is positioned to align the detector filter of the selected set of filtering elements with the camera the signal associated with the selected set of filtering elements activates the predetermined configuration of the camera for the selected set of filtering elements.

19. A portable medical examination apparatus comprising:
  (a) a head mountable frame;
  (b) an illumination source mounted on the frame, the illumination source configured to illuminate a tissue with radiation;
  (c) a detector mounted on the frame, the detector configured to collect radiation emanating from the tissue illuminated with the illumination source;
  (d) a pair of eye pieces mounted on the frame, the eye pieces configured to visualize the radiation emanating from the tissue illuminated with the illumination source;
  (e) a visor screen rotatable between an operable orientation and a non-operable orientation;
  (f) a first and a second set of filtering elements embedded in the visor screen, wherein each set of filtering elements includes an illumination filter, a detection filter and two eye piece filters in a fixed relationship to each other; and
  (g) a mechanism for reciprocating the visor screen between a first position and a second position, wherein when the visor screen is moved between the first position and the second position all of the filtering elements of the first and second set of filtering elements are simultaneous moved maintaining the fixed relationship of the filters within the first and second filtering set of filtering elements, wherein when the visor screen is in the operable orientation and in the first position the illumination filter of the first set of filtering elements is aligned with the illumination source such that the radiation generated by the illumination source passes through the illumination filter of the first set of filtering elements before illuminating the tissue, the detection filter of the first set of filtering elements is aligned with the detector such that the radiation emanating from the tissue passes through the detection filter of the first set of filtering elements before being collected by the detector, and the pair of eye piece filters of the first set of filtering elements is aligned with the pair of eye pieces such that the radiation emanating from the tissue passes through the pair of eye piece filters of the first set of filtering elements before passing to the eye pieces, and wherein when the visor screen is in the operable orientation and is moved to the second position the illumination filter of the second set of filtering elements is aligned with the illumination source such that the radiation generated by the illumination source passes through the illumination filter of the second set of filtering elements before illuminating the tissue, the detection filter of the second set of filtering elements is aligned with the detector such that the radiation emanating from the tissue passes through the detection filter of the second set of filtering elements before being collected by the detector, and the pair of eye piece filters of the second set of filtering elements is aligned with the pair of eye pieces such that the radiation emanating from the tissue passes through the pair of eye piece filters of the second set of filtering elements before passing through to the eye pieces.

20. The examination apparatus of claim 19, wherein the visor screen further embeds a first signal associated with the first set of filtering elements and a second signal associated with the second set of filtering elements, wherein the first signal enables a first configuration for the detector and the second signal enables a second configuration for the detector.

21. The examination apparatus of claim 19, wherein the illumination source includes a first light source and a second light source and wherein the visor screen embeds a first signal associated with the first set of filtering elements such that when the visor screen is in the first position the first signal enables the first light source and wherein the visor screen embeds a second signal associated with the second set of filtering elements such that when the visor screen is in the second position the second signal enables the second light source.

22. The examination apparatus of claim 19, wherein the mechanism for reciprocating the visor screen between the first and second position includes rotation of the visor to designated locations about a pivot shaft mounted on the frame.

23. The examination apparatus of claim 22, wherein the illumination source includes a first and a second LED and wherein rotation of the visor to a first designated location about the pivot shaft activates the first LED and rotation of the visor to a second designated location about the pivot shaft activates the second LED.

24. The examination apparatus of claim 22, wherein rotation of the visor to a first designated location about the pivot shaft activates a first operating condition of the illumination source and rotation of the visor to a second designated location about the pivot shaft activates a second operating condition of the illumination source.

25. The examination apparatus of claim 22, wherein rotation of the visor to a first designated location about the pivot shaft activates a first detector configuration and rotation of the visor to a second designated location about the pivot shaft activates a second detector configuration.

* * * * *